(12) United States Patent
Flaction

(10) Patent No.: US 9,536,134 B2
(45) Date of Patent: Jan. 3, 2017

(54) ATHLETIC PERFORMANCE MONITORING DEVICE

(75) Inventor: Patrick Flaction, Chandolin-Pres-Saviese (CH)

(73) Assignee: Myotest SA (CH)

( * ) Notice: Subject to any disclaimer, the term of this patent is extended or adjusted under 35 U.S.C. 154(b) by 43 days.

(21) Appl. No.: 14/125,489

(22) PCT Filed: Jun. 13, 2012

(86) PCT No.: PCT/EP2012/061223
§ 371 (c)(1),
(2), (4) Date: Jun. 4, 2014

(87) PCT Pub. No.: WO2012/171967
PCT Pub. Date: Dec. 20, 2012

(65) Prior Publication Data
US 2014/0277633 A1   Sep. 18, 2014

Related U.S. Application Data

(60) Provisional application No. 61/498,180, filed on Jun. 17, 2011.

(51) Int. Cl.
*A63F 9/24* (2006.01)
*G06K 9/00* (2006.01)
(Continued)

(52) U.S. Cl.
CPC ........... *G06K 9/00348* (2013.01); *G01S 19/19* (2013.01); *G06F 19/3481* (2013.01);
(Continued)

(58) Field of Classification Search
CPC .... G06F 17/40; A61B 5/1118; A61B 5/02438; A63B 24/0062; A63B 2225/20; A63B 2220/14; A63B 2024/0065; A63B 2220/22; A63B 2220/836; A63B 69/0028; A63B 2220/803; A63B 2230/00; G06K 9/00342; G06K 2009/00738; G06K 9/00348
See application file for complete search history.

(56) References Cited

U.S. PATENT DOCUMENTS

| 6,539,336 B1 | 3/2003 | Vock et al. |
| 2006/0136173 A1* | 6/2006 | Case et al. ..................... 702/182 |

(Continued)

FOREIGN PATENT DOCUMENTS

| WO | WO-2009021147 A1 | 2/2009 |
| WO | WO-2010025467 A1 | 3/2010 |

OTHER PUBLICATIONS

International Search Report dated Feb. 11, 2013, filed in International Application No. PCT/EP2012/061223.

*Primary Examiner* — Steve Rowland
(74) *Attorney, Agent, or Firm* — Blank Rome LLP

(57) ABSTRACT

The present invention provides an athletic performance monitoring device having an accelerometer configured such that it can be worn by a user close to the center of gravity of the athlete; and a processing system including a global positioning system. The accelerometer is further configured such that it can wirelessly communicate acceleration data, relating to the acceleration of the user, to the processing system. In addition, the processing system is configured such that it can request acceleration data from the accelerometer only when some events depending on the output of the global positioning system and/or on a clock are occurring. It can also process the acceleration data it receives from the accelerometer to provide athletic performance information. There is further provided a corresponding method for providing athletic performance information. There is also provided an accelerometer for use in an athletic performance monitoring device.

16 Claims, 4 Drawing Sheets

(51) Int. Cl.
    *G01S 19/19*     (2010.01)
    *G06F 19/00*     (2011.01)
    *A61B 5/11*     (2006.01)
    *A61B 5/22*     (2006.01)
    *A61B 5/00*     (2006.01)
    *H04M 1/725*     (2006.01)

(52) U.S. Cl.
    CPC ............ *A61B 5/1118* (2013.01); *A61B 5/1124* (2013.01); *A61B 5/222* (2013.01); *A61B 5/681* (2013.01); *A61B 2503/10* (2013.01); *H04M 1/7253* (2013.01); *H04M 2250/12* (2013.01)

(56) References Cited

U.S. PATENT DOCUMENTS

2006/0265187 A1*  11/2006  Vock et al. .................... 702/182
2011/0215934 A1*  9/2011  Boyd et al. ................. 340/573.1
2011/0215952 A1*  9/2011  Aria ........................ G06F 3/017
                                                          341/20

* cited by examiner

ATHLETIC PERFORMANCE MONITORING DEVICE

RELATED APPLICATION

This Application is a National Phase of PCT/EP 2012/061223. filed on Jun. 13, 2012. which claims the priority of U.S. Provisional Application No. 61/498,180, filed on Jun. 17, 2011. the entire contents of both of which are hereby incorporated by reference.

FIELD OF THE INVENTION

The present invention concerns an athletic performance monitoring device and in particular, but not exclusively, an athletic performance monitoring device which comprises a user-worn accelerometer to measure acceleration of the using athlete; and which uses the acceleration data to provide athletic performance information. There is also provided an accelerometer suitable for use in such an athletic performance monitoring device and a corresponding method for providing athletic performance information.

DESCRIPTION OF RELATED ART

Athletes of all sport tend to monitor aspects of their performance; for example strength, heat rate, speed. Monitoring these aspects over time allows the athlete to determine the effectiveness of his training program and helps an athlete to avoid burn-out or overtraining. Accurate monitoring of performance is essential to enable an athlete to be at their peak at a particular date e.g. race day.

There is much technology which enables athletes to monitor aspects of their performance. For example, stop watches which are used to measuring time, heart rate monitors which allow an athlete to monitor their heart rate during training; and GSP systems which allow an athlete to monitor the terrain, distance and altitude over which they have trained.

However, existing technology does not allow an athlete to monitor all aspects of their performance while training. For example, it is not possible for a runner to monitor accurately, using existing technology, aspects such as contact time; duration of stride; distance covered in a stride; stride length; stride frequency; vertical displacement of the center of gravity; take-off angle; reactivity; stiffness; efficiency; force contact; distance contact; landing angle; regularity, while he is running.

It is an aim of the present invention to mitigate at least some of the disadvantages associated with existing athletic performance monitoring technology.

BRIEF SUMMARY OF THE INVENTION

According to an aspect, these aims are achieved by means of an athletic performance monitoring device comprising, an accelerometer configured such that it can be worn by an athlete close to the center of gravity of the athlete; and a processing system in an athlete-worn device; wherein the accelerometer is further configured such that it can wirelessly communicate acceleration data, relating to the acceleration of the athlete, to the processing system, and wherein the processing system is configured such that it can request acceleration data from the accelerometer only when some events, and such that it can process the acceleration data it receives from the accelerometer to provide athletic performance information. There is further provided a corresponding method for providing athletic performance information. There is also provided an accelerometer for use in an athletic performance monitoring device.

The accelerometer is preferably configured such that it can be worn by an athlete at a position which is within 20 centimeter of the athlete's centre of gravity, at a fixed position relative to this center of gravity.

The processing system thus acts as a master while the accelerometer acts as a slave in a master-slave configuration. If the processing system does not request acceleration data from the accelerometer, the acceleration data are simply stored in a memory of the accelerometer. If the memory of the accelerometer is full, the oldest acceleration data will be erased and overwritten by newest acceleration data.

The some events may be one or more predetermined events. At least some of said events may depend on the output of said global positioning system.

At least some of said events may depend on the output of the altimeter. For example, acceleration data may be requested when a predefined altitude has been reached, or when a change of slope has been detected.

According to an aspect, these aims are also achieved by means of an athletic performance monitoring device comprising, a waist-worn accelerometer; a wristwatch in wireless connection with the wrist-worn accelerometer, for receiving and processing acceleration data transmitted by said waist-worn accelerometer, wherein said wristwatch further includes a satellite-based location based system.

The processing system may retrieve location and/or elevation data from a global positioning system (GPS) in the athlete-worn device. An athlete-worn device is a device which is configured such that it can be worn by the athlete.

The athlete-worn device may include an altimeter. The altimeter may be based on a GPS, on a pressure sensor, or on a combination of both.

The athlete-worn device may include an electronic clock module.

The processing system may be configured such that it can request acceleration data from the accelerometer at regular intervals when no other events are occurring. For example, when the runner is running on a flat track, or on a track with a constant slope, acceleration data may be requested at regular intervals.

The athletic performance information may comprise at least one of the group comprising: contact time; duration of stride; distance covered in a stride; stride length; stride frequency; vertical displacement of the center of gravity; take-off angle; reactivity; stiffness; efficiency; force contact; distance contact; landing angle; regularity; asymmetry.

"contact time" is time of contact of the foot with the ground at each stride.

"duration of stride" is time it takes to complete a stride.

"Speed" is the distance travelled per unit time.

"Stride length" is distance covered by the center of gravity of the runner during a single stride. Alternatively, the stride length could also indicate the distance between two consecutive points of contacts of one leg with the ground.

"Stride frequency" is the number of strides per unit of time.

"Vertical displacement" is the vertical distance that the center of gravity of the runner moves during a stride.

"Take-off angle" is the angle of the lower leg with the ground when the foot leaves the ground.

"Reactivity" is (flight time/contact time)

"Stiffness" is a measure of the flexibility of a muscle and is defined by (the maximum force exerted by the ground on the foot/the duration of time the maximum force is exerted).

"Efficiency" is any parameter which indicates whether one particular stride, or the average of a plurality of strides, are efficient, and if the energy involved by this stride is well translated into horizontal displacement. Energy could be based on the oscillation of the center of gravity of the runner during each stride.

"Force contact" is the force exerted by the ground on the foot.

"Distance contact" is the horizontal distance covered by the center of gravity of the runner while one foot is in contact with the ground.

"Landing angle" is the angle of the lower leg with the ground when it lands on the ground.

"Regularity" indicates a variation of a rate of exercising; for example a variation of the rate at which an athlete's foot strikes the ground. This parameter can be used, among other, to detect the athlete's fatigue at an early stage.

"Energy consumed" is the amount of energy (calories) used to complete an exercise e.g. to complete a stride or a series of strides.

"Symmetry" indicates a difference in one parameter of the left leg and one corresponding parameter of the right leg. For example, symmetry can indicate that the average stride length with the left leg is longer than the average stride length with the right leg. This can be used, among other, for detecting risk of injuries.

The athletic performance monitoring device could be operated to detect when an athlete is becoming tired before the athlete fatigues to a point whereby injuries are likely to occur. This could be achieved, for example, by means of monitoring the symmetry.

The accelerometer is preferably adapted to be worn by an athlete close to the center of gravity of the athlete. Preferably the accelerometer is adapted to be worn by an athlete at a fixed distance to the center of gravity of the athlete, preferably within 20 centimeter of the. Most preferably the accelerometer is adapted to be worn by an athlete at centre of gravity of the athlete. The adaptation could mean for example that the size, shape and weight of the accelerometer is adapted to be comfortably worn by the athlete, on his trunk, for example on his chest or even closer to the center of gravity, on the waist. The adaptation could also mean for example that the accelerometer comprises a belt, or can be associated with a belt, to fix it near to the center of gravity of the athlete. The accelerometer can also comprise a clip, or be associated with a clip, to fix it on the clothes of the athlete, close to the center of gravity of the athlete. The adaptation could also mean that the software in the accelerometer is adapted to base its computations on a measure of acceleration made close to the center of gravity of the athlete The accelerometer may include a computational processor, such as a processor, a DSP, a microcontroller, a FPGA etc. in order to process the measured acceleration data and to send processed acceleration data to the main processing device in the athlete-worn device. The acceleration data processing made by the computational processor within the accelerometer may include signal processing, such as noise filtering, averaging, DC compensation. The acceleration data processing made within the accelerometer may include projection into a different reference axis, for example projection of the acceleration data into a referential having one vertical direction. The acceleration data processing made within the accelerometer may include computing at least some of the above mentioned parameters.

The acceleration data processed by the computational processor within the accelerometer may be transmitted to the processing device in the athlete-worn device. Those parameters computed by the computational processor within the accelerometer and based on the (raw) acceleration data are still considered to be (processed) acceleration data. Processing acceleration data within the accelerometer reduces the amount of acceleration data to transmit to the athlete-worn device.

The processing device within the athlete-worn device computes athletic performance information from the acceleration data retrieved from the accelerometer. The processing device within the athlete-worn device may compute athletic performance information from raw acceleration data retrieved from the accelerometer. Alternatively, the processing device may compute athletic performance information from already pre-processed acceleration data retrieved from the athlete-worn device.

The global positioning system may be further configured to monitor a plurality of parameters relating to the environment and/or movement of the athlete, the plurality of parameters comprising at least one of the group comprising: the geographical position of the athlete, the heat rate of the athlete, speed of the athlete, distance an athlete has travelled, slope of the terrain on which the athlete is travelling, direction in which the athlete is travelling, direction changes of the athlete (for team sports etc), variation of speed of the athlete, etc.

The global positioning system may be configured such that target values for one or more parameters relating to the environment and/or movement of the athlete can be pre-defined by an athlete, and the global positioning system may be configurable to processes the acceleration data it receives from the accelerometer to provide athletic performance information only the parameters relating to the environment and/or movement which are monitored by the global positioning system match the target values.

The global positioning system may be further configured to receive data relating to the height and weight of an athlete and to use the height and weight data to provide athletic performance information.

The global positioning system may be configured to continuously request acceleration data from the accelerometer. The accelerometer may be configured to continuously provide the global positioning system with acceleration data. The global positioning system may be configured to request acceleration data from the accelerometer at intervals. The accelerometer may be configured to provide the global positioning system with acceleration data at intervals. Preferably the intervals will be 60 second intervals. Preferably the global positioning system requests acceleration data from the accelerometer only when required; for example during an ascent, descent, change of slope, etc. This allows the global positioning system to compute and deliver parameters depending on the situation, for example a measure of the stride length at ascent and a different measure at descent.

The length of the intervals may be dependent on the athletic performance information which is to be provided by the athletic performance monitoring device. The length of the intervals may be dependent on a change in the situation of an athlete; for example a change in the athlete's environment such as for example a change of slope, etc.

The accelerometer may comprise a memory which is configured to store at least 30 seconds of acceleration data. The accelerometer may comprise a memory which is configured to store between 10-30 seconds of acceleration data. Preferably the accelerometer will comprise a memory which is configured to store at least 160 seconds of acceleration data.

The global positioning system may further comprise a memory which can store athletic performance information. Preferably the global positioning system may further comprise a memory which can store athletic performance information which has been obtained from at least 50 athletic performance tests.

The athlete-worn device can be a wristwatch which can be worn on the wrist of an athlete. The athlete-worn device can be a different type of athlete worn device, such as a portable music player, a cell phone, etc. the athlete worn-device preferably includes a display for displaying athletic information, and/or a loudspeaker for acoustically reproducing athletic information. The athlete-worn device is distinct from the accelerometer, can be worn at a different place on the body, and can be connected with the accelerometer over a wireless link.

The device according to any one of the preceding claims wherein the accelerometer may be configured such that it can be secured to a garment of an athlete.

The accelerometer may comprise a clip means which enables the accelerometer to be secured to a garment of an athlete.

The accelerometer may be housed within a water-proof housing.

The athletic performance monitoring device is preferably configured such that it operably communicate with a smart phone, a tablet, a PDA etc. The athletic performance monitoring device may be configured such that it can download maps or routes. For example the athletic performance monitoring device could download maps or routes from a smart phone which is connected to the internet. The maps or routes may include exercise stations. These exercise stations may be virtual. Preferably, as a user follows a route the athletic performance monitoring device can operate to indicate the user to carry out predetermined exercises at predefined locations along the route. Additionally, the athletic performance monitoring device may be configured such that it can monitor the performance, or technique, of the user as they execute the exercises at each exercise station.

The device may further comprise a processor means which is configured to detect an activation signal when the device is turned off or in a standby mode and wherein the processor means initiates the device to operate when it detects an activation signal.

According to a further aspect of the present invention there is provided an accelerometer, configured such that it can be worn by an athlete, the accelerometer further configurable to communicate acceleration data relating to the acceleration of the athlete, to a global positioning system which is configured so that it can process the acceleration data it receives from the accelerometer to provide athletic performance information.

According to a further aspect of the present invention there is provided a method for providing athletic performance information, the method comprising the steps of; measuring the acceleration of an athlete using an accelerometer which is worn by the athlete, to provide acceleration data; communicating the acceleration data to a global positioning system; processing the acceleration data using the global positioning system to provide athletic performance information.

BRIEF DESCRIPTION OF THE DRAWINGS

The invention will be better understood with the aid of the description of an embodiment given by way of example only and illustrated by the figures, in which.

DETAILED DESCRIPTION OF POSSIBLE EMBODIMENTS OF THE INVENTION

Figure 1:
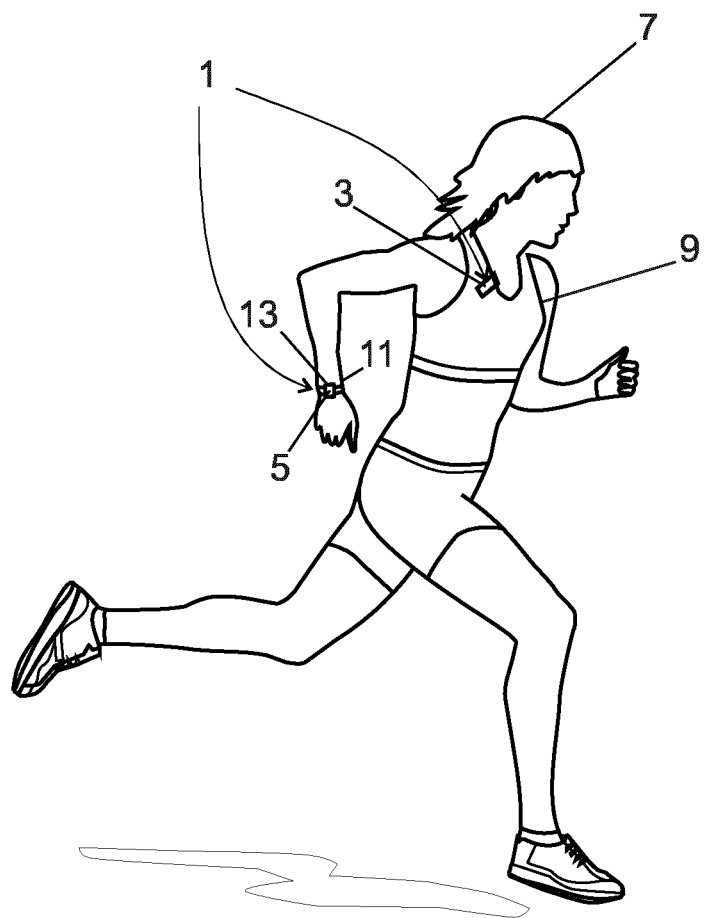
FIG. 1 shows a diagram of an athletic performance monitoring device according to an embodiment of the present invention, when in use.

FIG. 1 shows a diagram of an athletic performance monitoring device 1 according to an embodiment of the present invention, when in use. The device 1 comprises an accelerometer 3 and a processing system with a global position system 5 both of which are worn by an athlete 7. The processing system with a global position system 5 is in the form of a watch device; the athlete 7 therefore wears the global position system 5 around their wrist 11. The accelerometer 3 comprises a clip member (not shown) which enables the accelerometer 3 to be secured to a garment 9 (e.g. T-shirt) of the athlete 7, and in any case close to his center of gravity. Both the processing system 5 and the accelerometer 3 are small, and light, so that they can be comfortably worn by an athlete while exercising.

The processing system 5 may also comprise other sensors in addition or in replacement of the global position system. For example, the processing system in the athlete-worn device may include an altimeter, for example an altimeter based on a global position system, on a pressure sensor, or on a combination of both.

The accelerometer 3 is further configured such that it can wirelessly communicate with the processing system 5. The communication channel between the accelerometer 3 and the processing system 5 is carried out along a dedicated wirelessly channel, such as a Bluetooth, NFC, Zigbee or proprietary channel, so that interference with other devices cannot take place. The accelerometer 3 wirelessly communicates acceleration data, relating to the acceleration of the athlete 7, to the processing system 5. As will be described, the accelerometer 3 may include an acceleration sensor that deliver raw acceleration data, a computational processor 35 for pre-processing the raw acceleration data delivered by the acceleration sensor, and a memory 17 for storing raw and/or pre-processed acceleration data before transmission to the processing system 5.

The processing system 5 is configured to process the raw or pre-processed acceleration data it receives from the accelerometer 3 to provide athletic performance information. The athletic performance information is displayed on a display screen 13 of the processing system 5.

The accelerometer 3 is configured to continuously measure the acceleration of the athlete 7 as they exercise so that it can continuously provide and store acceleration data relating to the acceleration of the athlete 7 while the device 1 is operating. The processing system 5 may also be configured to continuously process the acceleration data it receives from the accelerometer 3 to provide athletic performance information. Thus, the athlete 7 is provided with athletic performance information as he exercises; in this particular example the athlete 7 is a runner so the runner is continuously provided with information relating to his running while they run.

The processing system is configured to act as a master while the accelerometer is configured to act as a slave in a master-slave configuration. This means that the accelerometer 3 does not transmit any acceleration data to the processing system unless requested to do so by the processing system 5. Acceleration data which can't be transmitted immediately are stored in a local memory of the accelerometer 3.

For the determination of certain athletic performance information the processing system 5 will not require continuously, up-to-date acceleration data from the accelerometer 3; certain athletic performance information can be determined by the processing system 5 using intermittent acceleration data. For this particular athletic performance information the processing system 5 may be configured to request acceleration data from the accelerometer 3 at intervals e.g at 60 second intervals. The length of the intervals may be dependent on the athletic performance information which is to be provided by the processing system 5. Depending on the athletic performance information which is to be determined and displayed by the processing system 5, the athlete 7 can configure the processing 5 so that it either continuously, or intermittently, receives acceleration data from the accelerometer 3.

The processing system 5 and the accelerometer 3 comprise a means to process the acceleration data to provide athletic performance information in the form of: contact time; duration of stride; distance covered in a stride; speed; stride length; stride frequency; vertical displacement; take-off angle; reactivity; stiffness; efficiency; force contact; distance contact; landing angle; regularity; symmetry; and energy consumed. This athletic performance information is continually updated by the processing system 5 using new acceleration data; thus the athletic performance information displayed on the display screen 13 of the processing system 5 will be continuously updated to reflect the athlete's 7 (runner's) current athletic performance.

The processing system 5 is also configured to monitor a plurality of parameters relating to the environment and/or movement of the athlete. For example, the processing system 5 can monitor the geographical position of the athlete, the heat rate of the athlete, speed of athlete, distance an athlete has travelled, slope of the terrain on which the athlete is travelling, altitude, and/or direction in which the athlete is travelling. The technical features required in the processing system 5 to enable it to monitor these parameters are well known in the art. For example, typically, in order to monitor the heart rate of the athlete 7 the processing system 5 will usually comprise a means for communicating with a heart rate monitor electrode worn by the athlete 7 around their chest. In order to monitor the altitude, the processing system will include an altimeter, for example an altimeter based on a GPS and/or on a pressure sensor.

The processing system 5 may be configured such that values of one or more parameters relating to the environment and/or movement of the athlete can be predefined by an athlete 7, and the processing system 5 may be configurable to processes raw or pre-processed acceleration data it receives from the accelerometer 3 to provide athletic performance information only when the parameters relating to the environment and/or movement which are monitored by the processing system 5 match pre-set parameters relating to the environment and/or movement parameters.

Additionally, the processing system 5 may be further configured to receive data relating to the height and weight of the athlete 7 and to use the height and weight data to provide certain athletic performance information. Typically, this height and weight data may be entered manually into the processing system 5.

Figure 2:
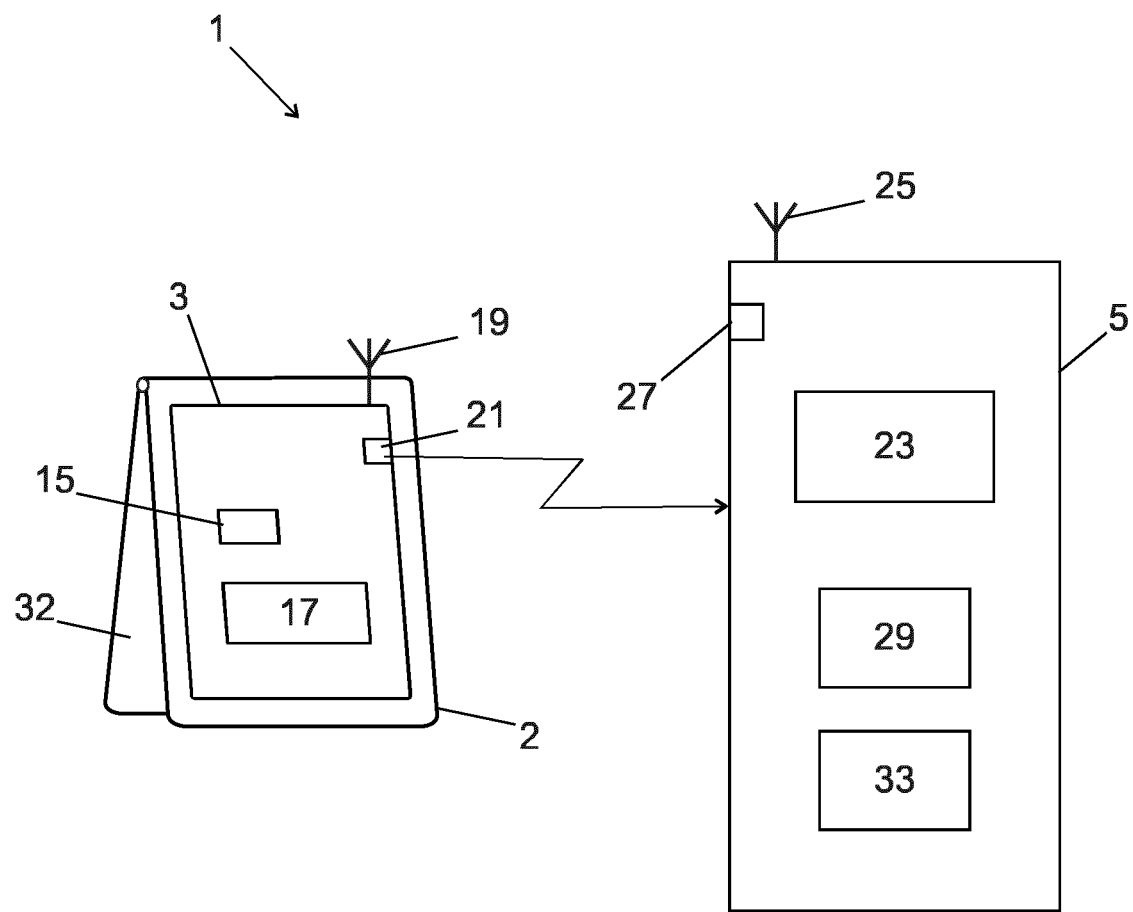
FIG. 2 is a schematic diagram of the components of the athletic performance monitoring device shown in FIG. 1.

FIG. 2 provides a schematic diagram, illustrating the components of the device 1 shown in FIG. 1; the accelerometer 3 and processing system 5 are shown in detail in FIG. 2.

The accelerometer 3 comprises an acceleration measuring means 15 (acceleration sensor) which is operable to measure the acceleration of the athlete 7 to provide acceleration data. In this particular example the accelerometer 3 may comprise a computational processor 35 which can carry out computations using measured acceleration values, to provide other useful the athletic performance information. The accelerometer 3 further comprises memory 17 which is configured to store acceleration data; in this particular example the memory is configured to store at least 160 seconds of acceleration data. However, the memory 17 may be configured to store any amount of acceleration data. The memory may also store pre-processed acceleration data.

The accelerometer 3 further comprises a transmitter 19 and receiver 21 which are configured to communicate with the global positioning system 5. The transmitter 19 is used to communicate the acceleration data to the global positioning system 5.

The accelerometer 3 is preferably housed within a waterproof housing 31. The water proof housing will protect the accelerometer 3, prolonging its lifespan, and enabling it to be used in all weather conditions. The clip member 32, which is used to secure the accelerometer 3 to a garment 9 (e.g. T-shirt) of the athlete 7, is also shown in FIG. 2.

The processing system 5 with the global position system and/or other sensors is shown to comprise a processor 23 which is configured such that it can process acceleration data transmitted to the global positioning system 5 from the accelerometer 3. The processor 23 is configured such that it can process acceleration data to provide athletic performance information in the form of: contact time; duration of stride; distance covered in a stride; speed; stride length; stride frequency; vertical displacement; take-off angle; reactivity; stiffness; efficiency; force contact; distance contact; landing angle; regularity; and energy consumed. The processor 23 may also need to take into account the parameters relating to the environment and/or movement of the athlete which are detected by the global positioning system 5, to provide certain athletic performance information; for example, processor 23 may take into account the geographical position of the athlete, the heat rate of the athlete, speed of athlete, distance an athlete has travelled, slope of the terrain on which the athlete is travelling, direction in which the athlete is travelling, to provide athletic performance information. Table 1 lists the athletic performance information which can be provided by the processor 23 in the processing system 5 and the calculations used to determine this athletic performance information:

TABLE 1

| Name | Description |
| --- | --- |
| Version | Results block version |
| ContactTime | Contact time in ms |

TABLE 1-continued

| Name | Description |
| --- | --- |
| Duration | Duration in s |
| Distance | Distance in m |
| Speed | Speed in m/s * 1000 |
| StrideLength | Stride length in mm |
| Frequency | Stride per second in Hz * 1000 |
| VerticalDisplacment | Vertical undulation of the gravity center in mm |
| TakeOffAngle | Take off angle in Degree * 100 |
| Reactivity | Reactivity index * 1000 |
| Stiffness | Muscle stiffness in kN/m |
| Efficiency | Efficiency index |
| FContact | Force over contact time in body weight * 100 |
| DistanceContact | Distance over contact time in mm |
| LandingAngle | Leg landing angle in Degree * 100 |
| Regularity | Regularity index in % * 100 |
| EnergyConsumed | Energy consumed for 1 km in kcal |
| FeetCTDiff | Contact time difference between feet in ms |
| Assymetry | Difference of one parameter (left - right or front-back) |

The athletic performance information outlined in table 1 may be indicated separately for different conditions, for example for different slopes.

The processing system 5 may be configured such that target values for one or more parameters relating to the environment and/or movement of the athlete can be predefined by an athlete or at factory, and the processing system 5 is configurable to processes the acceleration data it receives from the accelerometer 3 to provide athletic performance information only when the parameters relating to the environment and/or movement which are monitored by the global positioning system match those predefined target values.

The processing system further comprises one or a plurality of sensors, for example a global position system (GPS), an altimeter, a clock, and other sensors. Those sensors may be housed within the athlete-worn device, or alternatively connected to this athlete-worn device. Those sensors generate sensor data, such as positioning data, elevation data, time data, heart rate data, which may be compared with target values to define when acceleration must be retrieved from the accelerometer.

The processing system 5 is further provided with a memory 29 which can store athletic performance information. In this particular example the memory 29 can store athletic performance information which has been obtained from at least fifty athletic performance tests; however it will be understood that the memory 29 can be configured to store any amount of athletic performance information.

The processing system 5 also comprises a transmitter 25 and receiver 27 which are configured to communicate with the accelerometer 3. The receiver 27 is used to receive acceleration data from the accelerometer 3.

The processing system 5 further comprise a processor means 33 which, when the device 1 is turned off or in a standby mode, is configured to monitor for an activation signal. The athlete 7 can generate an activation signal by pressing an "activation" button or "on" button which is provided on the global positioning system 5 or on the accelerometer 3. When the processor means 33 detects an activation signal it initiates the device 1 to begin operation. Alternatively, or additionally a similar processor means may be provided in the accelerometer 3.

According to a further aspect of the present invention there is provided a method for providing athletic performance information, the method comprising the steps of; measuring the acceleration of an athlete using an accelerometer which is worn by the athlete, to provide acceleration data; communicating the acceleration data to a processing system in a athlete-worn device; processing the acceleration data using the processing system to provide athletic performance information.

In use, the device 1 is powered up by an athlete pressing for example an "activation" or "on" button. Pressing the "activation" or "on" button generates an activation signal which the processor means 33 detects. The processor means 33 initiates the device 1 to begin operation.

Figure 3:
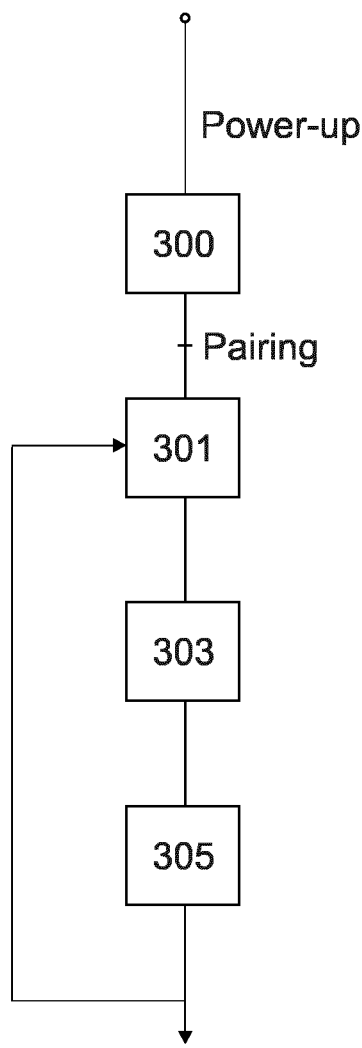
FIG. 3 provides a flow diagram of the operational steps carried out by the accelerometer of the device of FIG. 1, when in use.

FIG. 3 provides a flow diagram of the operational steps carried out by the accelerometer 3 during operation. Once powered up (300) the accelerometer 3 establishing communication with the global positioning system 5 (pairing). The athlete 7 should then begin to exercise e.g. running. The accelerometer 3 measures the acceleration of the athlete 7 using the acceleration measuring means 15, to provide acceleration data (301). Additionally, computations may be carried out on the acceleration measurements by the computational processor 35 to provide other useful athletic performance information, i.e., pre-processed acceleration data (303). Once the computations are completed the acceleration data (raw data and/or pre-processed data) are stored in the memory 17 of the accelerometer 3 (305). On request from the processing system, the last acceleration data stored in the memory are then wirelessly sent to the processing system 5.

In the processing system 5 the acceleration data is processed to provide athletic performance information which is displayed on the display screen 13 of the processing system 5, and/or displayed by another device, and/or audibly to the athlete as an acoustic signal.

Figure 4:
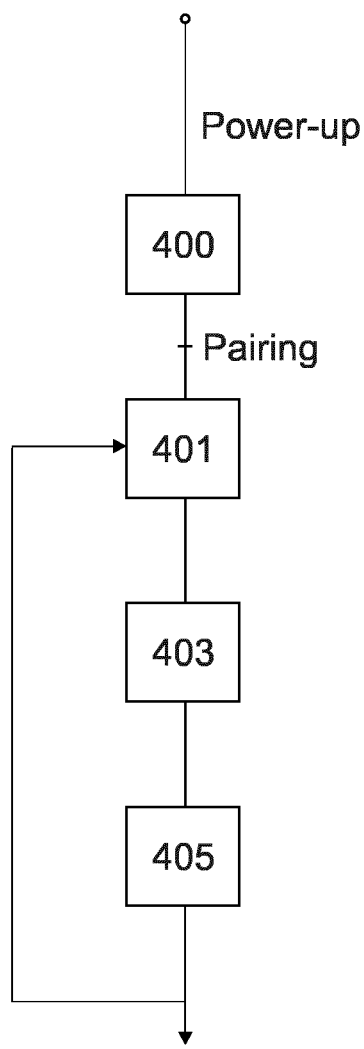
FIG. 4 provides a flow diagram of the operational steps carried out by the global positioning system of the device of FIG. 1, when in use.

FIG. 4 provides a flow diagram of the operational steps carried out by the processing system 5 during operation. Once the processing system 5 is powered up (400) the processing system 5 establishes communication with the accelerometer 3 (pairing). The athlete 7 can then begin to exercise e.g. running. While the accelerometer 3 measure the acceleration of the athlete 7 during exercise, the processing system 5 measures various parameters relating to the environment and/or movement of the athlete, for example, the geographical position of the athlete, the altitude of the athlete, the heat rate of the athlete, speed of the athlete, distance an athlete has travelled, slope of the terrain on which the athlete is travelling, direction in which the athlete is travelling; time (401).

When a particular event is detected based on at least one of those parameters, the processing system 5 sends a request to the accelerometer to retrieve the latest acceleration data, for example raw and/or pre-processed data corresponding to one particular interval.

The processing system 5 then receives the requested acceleration data from the accelerometer 3. Using the parameters relating to the environment and/or movement of the athlete which the global positioning system 5 has measured and acceleration data provided by the accelerometer 3, the processor 23 within the global positioning system 5 processes provide athletic performance information in the form of: contact time; duration of stride; distance covered in a stride; speed; stride length; stride frequency; vertical displacement; take-off angle; reactivity; stiffness; efficiency; force contact; distance contact; landing angle; regularity; symmetry; and/or energy consumed (403). This athletic performance information is displayed on the display screen of the global positioning system 5 and stored in the memory 29 of the processing system 5 (405).

In one embodiment, acceleration data is transmitted in pre-processed form from the accelerometer to the processing system in the athlete-worn device each time when the processing system detects from the altimeter a new and significant change in slope; for example, after the runner starts climbing, or after the runner starts descending. If no change in slope is detected during a predetermined amount of time, for example 30 seconds or one minute, acceleration data will be requested. In this way, acceleration data will be retrieved at least once during each predetermined amount of time, and more often when an event, such as a change in slope, has been detected from the altimeter.

The acceleration data retrieved from the accelerometer after an event detection may be time shifted relatively to the detection of the event. For example, if an event such as a change in slope has been detected, the processing system may want to retrieve acceleration data at the exact moment of this event (for example when the change in slope did occur), or during a period after this event (for example the 20 seconds after the change in slope).

Various modifications and variations to the described embodiments of the invention will be apparent to those skilled in the art without departing from the scope of the invention as defined in the appended claims. Although the invention has been described in connection with specific preferred embodiments, it should be understood that the invention as claimed should not be unduly limited to such specific embodiment.

The invention claimed is:

1. An athletic performance monitoring device comprising:
   an accelerometer adapted to be worn by an athlete close to the center of gravity of the athlete; and
   a user-worn device with a processing system integral thereto such that the processing system can be worn by the athlete;
   wherein the accelerometer is further configured such that it can wirelessly communicate acceleration data, relating to the acceleration of the athlete, to the processing system, and wherein the processing system is configured such that, during use, it requests acceleration data from the accelerometer only when a predefined event has occurred, and such that it can process the acceleration data it receives from the accelerometer to provide athletic performance information.

2. The athletic performance monitoring device according to claim 1, wherein said athlete-worn device includes a global positioning system,
   and wherein at least some of said predefined event depends on the output of said global positioning system.

3. The athletic performance monitoring device according to claim 1, wherein said athlete-worn device includes an altimeter,
   and wherein at least some of said predefined event depends on the output of said altimeter.

4. The athletic performance monitoring device according to claim 2, wherein said athlete-worn device includes an electronic clock module,
   and wherein said predefined event includes an inactive event wherein the inactive event is an event defined by when none of one or more selected predefined events occurring.

5. The athletic performance monitoring device according to claim 1, wherein the athletic performance information comprises at least one of the group comprising: contact time; duration of stride; distance covered in a stride; speed; stride length; stride frequency; vertical displacement of the center of gravity; take-off angle; reactivity; stiffness; efficiency; force contact; distance contact; landing angle; regularity.

6. The athletic performance monitoring device according to claim 1, wherein the processing system is further configured to monitor a plurality of parameters relating to an environment and/or movement of the athlete, the plurality of parameters comprising at least one of the group comprising: the geographical position of the user, the heat rate of the athlete, speed of the user, distance an athlete has travelled, slope of the terrain on which the athlete is travelling, direction in which the athlete is travelling.

7. The athletic performance monitoring device according to claim 6, wherein the processing system is configured such that target values for one or more parameters relating to the environment and/or movement of the athlete can be pre-defined by the athlete, and the processing system is configured to processes the acceleration data it receives from the accelerometer to provide athletic performance information only when the parameters relating to the environment and/or movement Which are monitored by a global positioning system match the target values.

8. The athletic performance monitoring device according to claim 1, wherein the processing system is configured to request acceleration data from the accelerometer at intervals.

9. The athletic performance monitoring device according to claim 8, wherein the length of the intervals are dependent on the athletic performance information which is to be provided by the athletic performance monitoring device.

10. The athletic performance monitoring device according to claim 1, wherein the processing system is configured to request acceleration data from the accelerometer when the global positioning system detects a change in a predefined aspect of an environment of the athlete.

11. The athletic performance monitoring device according to claim 10, wherein the processing system is configured to request acceleration data from the accelerometer when the global positioning system detects a change in slope.

12. The athletic performance monitoring device according to claim 11 wherein, the processing system is configured to provide athletic performance information depending on the slope, so that athletic performance information associated with different slopes, is provided.

13. The athletic performance monitoring device according to claim 1, wherein the accelerometer is configured such that it can be secured to a garment of an athlete.

14. A method for providing athletic performance information, the method comprising the steps of;
   measuring the acceleration of an athlete using an accelerometer adapted to be worn by the athlete close to the center of gravity of the athlete, to provide acceleration data;
   wirelessly communicating by the accelerometer the acceleration data, relating to the acceleration of the athlete, to a processing system integral in an athlete-worn device being worn by the athlete, wherein the processing system is configured such that, during use, it requests acceleration data from the accelerometer only when a predefined event has occurred;
   processing by the processing system the acceleration data the processing system receives from the accelerometer, to provide athletic performance information.

15. An athletic performance monitoring device comprising:
   an accelerometer adapted to he worn by an athlete close to a center of gravity of the athlete; and
   a user-worn device with a processing system;

wherein the accelerometer is further configured such that it can wirelessly communicate acceleration data, relating to the acceleration of the athlete, to the processing system, and wherein the processing system is configured to be a master and the accelerometer is configured to be a slave in a master-slave configuration, such that the accelerometer sends acceleration data to the processing system only upon receiving a request from the processing system, and wherein the processing system is configured such that it can request acceleration data from the accelerometer only when a predefined event has occurred, and such that it can process the acceleration data it receives from the accelerometer to provide athletic performance information.

16. An athletic performance monitoring device comprising:

an accelerometer adapted to be worn by an athlete close to the center of gravity of the athlete; and a user-worn device with a processing system;

wherein the accelerometer is further configured such that it can wirelessly communicate acceleration data, relating to the acceleration of the athlete, to the processing system, and wherein the processing system is configured such that it can request acceleration data from the accelerometer only when a predefined event has occurred, and such that it can process the acceleration data it receives from the accelerometer to provide athletic performance information, wherein, the processing system is configured to provide athletic performance information depending on the slope, so that athletic performance information associated with different slopes, is provided.

* * * * *